United States Patent
Itchoda et al.

(10) Patent No.: US 10,513,685 B2
(45) Date of Patent: Dec. 24, 2019

(54) METHOD FOR DIFFERENTIATING PLURIPOTENT MAMMALIAN STEM CELLS INTO A POPULATION OF HEPATIC CELLS IN A MICROCHAMBER

(75) Inventors: Yoko Itchoda, Ibaraki (JP); Go Tazaki, Ibaraki (JP); Masaya Hosoda, Ibaraki (JP); Motohiro Fukuda, Ibaraki (JP); Hideki Taniguchi, Kanagawa (JP); Yun-Wen Zheng, Kanagawa (JP); Keisuke Sekine, Kanagawa (JP)

(73) Assignees: CORNING INCORPORATED, Corning, NY (US); PUBLIC UNIVERSITY CORPORATION YOKOHAMA CITY UNIVERSITY, Yokohama-Shi, Kanagawa (JP)

( * ) Notice: Subject to any disclaimer, the term of this patent is extended or adjusted under 35 U.S.C. 154(b) by 0 days.

(21) Appl. No.: 13/636,855

(22) PCT Filed: Mar. 23, 2011

(86) PCT No.: PCT/JP2011/001708
§ 371 (c)(1),
(2), (4) Date: Nov. 30, 2012

(87) PCT Pub. No.: WO2011/118211
PCT Pub. Date: Sep. 29, 2011

(65) Prior Publication Data
US 2013/0071932 A1 Mar. 21, 2013

(30) Foreign Application Priority Data
Mar. 23, 2010 (JP) ................................. 2010-066324

(51) Int. Cl.
*C12N 5/071* (2010.01)
*C12N 5/0735* (2010.01)
*C12M 1/32* (2006.01)

(52) U.S. Cl.
CPC ........... *C12N 5/0606* (2013.01); *C12M 23/12* (2013.01); *C12N 2502/28* (2013.01); *C12N 2506/02* (2013.01); *C12N 2535/10* (2013.01)

(58) Field of Classification Search
CPC .............. C12N 5/0606; C12N 2502/28; C12N 2506/02; C12N 2535/10; C12M 23/12
See application file for complete search history.

(56) References Cited

U.S. PATENT DOCUMENTS

| | | |
|---|---|---|
| 8,470,600 B2 | 6/2013 | Duch et al. |
| 2007/0281355 A1 * | 12/2007 | Dalton et al. ................. 435/377 |
| 2008/0026460 A1 | 1/2008 | Palecek et al. |
| 2010/0190253 A1 | 7/2010 | Tazaki et al. |
| 2011/0212061 A1 | 9/2011 | Keller et al. |
| 2011/0318829 A1 | 12/2011 | Tazaki et al. |
| 2013/0071932 A1 | 3/2013 | Itchoda et al. |

FOREIGN PATENT DOCUMENTS

| | | | |
|---|---|---|---|
| DE | 10 2009 002 577 A1 | 10/2010 | |
| EP | 2 551 341 | 1/2013 | |
| JP | 2003-530879 | 10/2003 | |
| JP | 2007 61096 | 3/2007 | |
| JP | 2008 509676 | 4/2008 | |
| JP | 2008-546414 | 12/2008 | |
| TW | 200804588 | 1/2008 | |
| TW | 200907053 A | 2/2009 | |
| WO | 2006/020919 | 2/2006 | |
| WO | 2006/082890 | 8/2006 | |
| WO | 2007/002385 | 1/2007 | |
| WO | 2008 156041 | 12/2008 | |
| WO | WO 2008156041 A1 * | 12/2008 | |
| WO | WO 2009099152 A1 * | 8/2009 | ............ C12M 23/12 |
| WO | 2010 047132 | 4/2010 | |
| WO | WO 2010/0122044 A2 | 10/2010 | |

OTHER PUBLICATIONS

Bauwens et al. "Control of Human Embryonic Stem Cell Colony and Aggregate Size Heterogeneity Influences Differentiation Trajectories." Stem Cells. Sep. 2008;26(9):2300-10.*
Valdimarsdottir et al. "Functions of the TGFbeta superfamily in human embryonic stem cells." APMIS. (2005);113(11-12):pp. 773-89.*
D'Amour et al. "Efficient differentiation of human embryonic stem cells to definitive endoderm." Nature Biotechnology (Dec. 2005); 23(12): pp. 1534-1541.*
Si-Tayeb et al. "Highly Efficient Generation of Human Hepatocyte-Like Cells from Induced Pluripotent Stem Cells." Hepatology (E-published Oct. 2009); 51(1): pp. 297-305.*
Tazaki et al. English Translation of JP2008/156041 (Specification), Dec. 2008.*
Tazaki et al. English Translation of JP2008/156041 (Drawings), Dec. 2008.*
Kurosawa, H. "Methods for inducing embryoid body formation: in vitro differentiation system of embryonic stem cells." J Biosci Bioeng. May 2007;103(5):389-98.*
Vackova et al. "Putative embryonic stem cell lines from pig embryos." J Reprod Dev. Dec. 2007;53(6):1137-49. (Year: 2007).*
Cao et al. "In vitro differentiation of rat embryonic stem cells into functional cardiomyocytes" Cell Res. Sep. 2011;21(9):1316-31. (Year: 2011).*

(Continued)

*Primary Examiner* — Titilayo Moloye

(57) ABSTRACT

Provided is a method that achieves control of embryoid body size and can induce differentiation in a state where the embryoid body size is controlled, by using a cell culture chamber having a plurality of microchambers formed therein. A culture method for causing differentiation of pluripotent mammalian cells uses a cell culture chamber (10) having a plurality of microchambers (11) formed on a culture surface. The cell culture chamber (10) has a culture surface formed of spaces in which the microchambers (11) have a space structure with a height of 10 μm to 500 μm and a bottom area of 100 μm² to 1 mm². The culture method for causing differentiation of pluripotent mammalian cells includes culturing pluripotent mammalian cells to obtain a cell population at least partially differentiated into endoderm lineage cells, by using the cell culture chambers (10).

23 Claims, 4 Drawing Sheets

(56) References Cited

OTHER PUBLICATIONS

Honda et al. "Stable embryonic stem cell lines in rabbits: potential small animal models for human research." Reprod Biomed Online. Nov. 2008;17(5):706-15. (Year: 2008).*

Li et al. "Horse embryonic stem cell lines from the proliferation of inner cell mass cells." Stem Cells Dev. Aug. 2006;15(4):523-31 (Year: 2006).*

Pera et al. "Differentiation of human pluripotent teratocarcinoma stem cells induced by bone morphogenetic protein-2." Reprod Fertil Dev. 1998;10(7-8):551-5. (Year: 1998).*

Schuldiner et al. "Effects of eight growth factors on the differentiation of cells derived from human embryonic stem cells" (Year: 2000).*

Bauwens, C.L., et al., "Control of Human Embryonic Stem Cell Colony and Aggregate Size Heterogeneity Influences Differentiation Trajectories," Stem Cells, vol. 26, pp. 2300-2310, (2008).

Hudson, C., et al., "Xsox17α and -β Mediate Endoderm Formation in Xenopus," Cell, vol. 91, pp. 397-405, (Oct. 31, 1997).

International Search Report dated Jun. 21, 2011 in PCT/JP11/01708 Filed Mar. 23, 2011.

Yu-Shik Hwang, et al. "Microwell-mediated control of embryoid body size regulates embryonic stem cell fate via differential expression of WNT5a and WNT11" Proceedings of the National Academy of Sciences, vol. 106, No. 40, XP-55067093A, Oct. 6, 2009, pp. 16978-16983.

Hannes-Christian Moeller, et al. "A microwell array system for stem cell culture" Biomaterials, Elsevier Science Publishers BV, Barking, GB, vol. 29, No. 6, XP-22371128A, Nov. 14, 2007, pp. 752-763.

Yu-Shik Hwang, et al., "Microwell-mediated control of embryoid body size regulates embryonic stem cell fate via differential expression of WNT5a and WNT11", Proc. Natl. Acad. Sci. U.S. A., Oct. 6, 2009, 106(40), p. 16978-83, EPub Sep. 23, 2009.

Ryoko Chinzei, et al., "Embryoid-Body Cells Derived From a Mouse Embryonic Stem Cell Line Show Differentiation Into Functional Hepatocytes", Hepatology,, Jul. 2002, 36(1), p. 22-9.

Toshihiko Ezashi, et al., "Low $O_2$ Tensions and the prevention of differentiation of hES cells", Proc. Natl. Acad. Sci. U.S.A., Mar. 29, 2005, 102(13), p. 4783-8, Epup Mar. 16, 2005.

Office Action as received in the corresponding China Patent Application No. 201180015440.9 dated Apr. 17, 2015 w/English Translation.

Office Action as received in the corresponding Japanese Patent Application No. 2012-506851 dated May 26, 2015 w/English Translation.

Chinese Office Action dated Nov. 4, 2015 in Patent Application No. 201180015440.9 (with Partial English Translation).

Written Opinion & Search Report dated Sep. 5, 2016 in the corresponding Singapore Patent Application No. 10201502242V.

Yoon Young Choi, et al., "Controlled-size embryoid body formation in concave microwell arrays", Biomaterials, Mar. 5, 2010, vol. 31, pp. 4296-4303.

Masaya Iwamuro, et al., Establishment of an effective method of differentiating hepatocytes from an iPS cell using a basal lamina matrix, regenerative medicine, Feb. 5, 2010, vol. 9, Suppl., 164 0-05-5 w/English Translation.

Dismissal of Re-examination before Appeal issued on Jun. 7, 2016 in the corresponding Japan Patent Application No. 2012-606851 w/Partial English Translation.

Office Action as received in the corresponding Japanese Patent Application No. 2012-506851 with partial English translation dated Feb. 21, 2017.

Office Action as received in the corresponding Canada Patent Application No. 2,793,971 dated Jan. 27, 2017.

Office Action as received in the corresponding Korean Patent Application No. 10-2012-7027302 dated Jul. 25, 2017 w/ English Translation.

Written Opinion as received in the corresponding Singapore Patent Application No. 10201502242V dated Oct. 9, 2017.

Baharvand H. et al., "Differentiation of human embryonic stem cells into hepatocytes in 2D and 3D culture systems in vitro", Int.. J. Dev. Biol. 50: 645-652 (2006).

Khademhosseini et al. "Molded polyethylene glycol microstructures for capturing cells within microfluidic channels" , Lab Chip 4:425-430, Oct. 2004.

Sekine et al. "Highly efficient generation of definitive endoderm lineage from human induced pluripotent stem cells" , Transplantation Proceedings 44(4) 2012, pp. 1127-1129.

CA2793971 Office Action dated Feb. 12, 2019, Canada Patent Office, 5 Pgs.

* cited by examiner

METHOD FOR DIFFERENTIATING PLURIPOTENT MAMMALIAN STEM CELLS INTO A POPULATION OF HEPATIC CELLS IN A MICROCHAMBER

This application is a National Stage of PCT/JP11/001708 filed Mar. 23, 2011 and claims the benefit of JP 2010-066324 filed Mar. 23, 2010.

TECHNICAL FIELD

The present invention relates to culture of pluripotent cells, and more particularly, to a culture method for causing differentiation of pluripotent mammalian cells.

BACKGROUND ART

A technique of using cells isolated from a tissue in testing or examination is an essential method in the biotechnology-related fields. It is widely used in diagnosing a disease or pathological condition, searching for a new drug and evaluating the efficacy of a drug, or in animal inspection, plant inspection, testing for environmental pollutants, and so on. Thus, cells and the like used in the biotechnology field have been greatly diversified.

In recent years, studies on pluripotent cells, such as embryonic stem cells (ES cells) and induced pluripotent stem cells (iPS cells), have been conducted. The pluripotent cells are cells that can differentiate into all types of cells constituting tissues, parts, and organs which form living organisms. ES cells are used as a potent model system for studying a mechanism underlying the biological properties of pluripotent cells and differentiation in the early embryo. This provides opportunities for genetic operation of mammals and resulting application of business, medicine, and agriculture. Further, techniques for diagnosing a disease or pathological condition, searching for a new drug, and evaluating the efficacy of a drug have been developed by using the appropriate proliferation and differentiation of ES cells.

The isolated cells are sometimes used immediately for testing, but in many cases, operations for causing proliferation and differentiation of cells in a culture dish or a test tube are carrier out. Various examinations are carried out using the cultured cells. Isolated pluripotent cells are required to show drug susceptibility and toxic reaction that are similar to those obtained in a test performed in a living body, that is, a so-called in vivo test, and are also required to differentiate into target cells with high efficiency.

However, the biochemical mechanism for controlling the pluripotency and differentiation of pluripotent cells is barely understood to date. For example, Patent Literature 1 discloses compositions and methods for the production of differentiated mammalian cells as means for causing differentiation of pluripotent cells. Specifically, Patent Literature 1 discloses a cell differentiation method that employs the technique of culturing cells on a feeder layer or under non-feeder conditions in a cell culture, and contacting mammalian cells with an inhibitor of the PI3-kinase signaling pathway and a member of the TGFb family to generate the mammalian cells differentiated from pluripotent mammalian stem cells.

In addition to the methods disclosed above, Non Patent Literature 1 discloses that the differentiation efficiency of pluripotent cells is changed depending on the size of an aggregate of embryoid bodies. Thus, it is an extremely important factor to control the size of the aggregate so as to obtain a uniform endoderm lineage cell, or cells differentiated from the cell, such as hepatic cells or β cells. According to the method disclosed in Non Patent Literature 1, Matrigel having cell adhesion properties and having a diameter of several tens of μm to several hundreds of μm is arranged at regular intervals on a culture bottom surface, thereby forming a cell adhesive region. Cell non-adhesive polymers are coated around the cell adhesive region to allow cells to selectively adhere to the cell adhesive region, thereby controlling the size of an aggregate of embryoid bodies.

CITATION LIST

Patent Literature

Patent Literature 1: Published Japanese Translation of PCT International Publication for Patent Application, No. 2008-509676

Non Patent Literature

Non Patent Literature 1: "Control of Human Embryonic Stem Cell Colony and Aggregate Size Heterogeneity Influences Differentiation Trajectories" written by Celine Liu Bauwens, Raheem Peerani, Sylvia Niebruegge, kimberly a. Woodhouse, Eugenia Kumacheva, Mansoor Husain, and Peter W. Zandstra, STEM CELLS 2008; 26, pp. 2300-2310

SUMMARY OF INVENTION

Technical Problem

However, the culture method disclosed in Non Patent Literature has a problem that the operation is complicated and the cost is high. In addition, some cells may adhere to a cell non-adhesive portion during a culture period, which hinders differentiation of cells with high efficiency. This makes it difficult to control the size of an aggregate of embryoid bodies.

In view of such circumstances, it is an object of the present invention to provide a method that achieves control of embryoid body size and can induce differentiation in a state where the embryoid body size is controlled, by using a cell culture chamber including a plurality of microchambers formed on a surface, the cell culture chamber having a culture surface formed of spaces in which the microchambers have a bottom area of 100 μm$^2$ to 1 mm$^2$ and a depth of 10 μm to 500 μm.

Solution to Problem

An aspect of the present invention is a culture method for causing differentiation of pluripotent mammalian cells by using a cell culture chamber including a plurality of microchambers formed on a culture surface. The cell culture chamber has a culture surface formed of spaces in which a space structure of each of the microchambers has a height of 10 μm to 500 μm and a bottom area of 100 μm$^2$ to 1 mm$^2$. The culture method for causing differentiation of pluripotent mammalian cells includes culturing pluripotent mammalian cells to obtain a cell population at least partially differentiated into endoderm lineage cells, by using the cell culture chamber. The size of each embryoid body to be cultured is controlled using the microchambers. The differentiation of cells is induced using the state where the embryoid body size is controlled. Consequently, the effect of differentiating pluripotent mammalian cells is improved.

Further, in the culture method for causing differentiation of pluripotent mammalian cells according to an aspect of the present invention, pluripotent mammalian cells are preferably selected from the group consisting of embryonic stem cells (ES cells), induced pluripotent stem cells (iPS cells), teratocarcinoma cells, and sperm stem cells. It is preferable to seed and culture 1 to $3\times10^5$ pluripotent mammalian cells in one of the microchambers to obtain the cell population.

In the culture method for causing differentiation of pluripotent mammalian cells according to one aspect of the present invention, the pluripotent mammalian cells are preferably cultured in a culture medium including one kind or a mixture of two or more kinds selected from the group consisting of a TGF-β family, an FGF family, and a PI3-kinase signaling pathway inhibitor. A member of the TGF-β family described above is preferably one kind or a mixture of two or more kinds selected from the group consisting of Nodal, Activin A, Activin B, TGF-β, BMP2, and BMP4. A member of the FGF family described above is preferably one kind or a mixture of two or more kinds selected from the group consisting of b-FGF, FGF-4, and FGF-2. The PI3-kinase signaling pathway inhibitor described above is preferably one kind or a mixture of two or more kinds selected from the group consisting of LY294002, rapamycin, wortmannin, lithium chloride, Akt inhibitor I, Akt inhibitor II, Akt inhibitor III, and NL-71-101.

Further, the culture method for causing differentiation of pluripotent mammalian cells according to an aspect of the present invention includes one of: (1) obtaining a cell population in which SOX17 is at least partially expressed and AFP is not expressed; (2) obtaining a cell population in which SOX17 is at least partially expressed and Pdx-1 is not expressed; (3) obtaining a cell population in which one of FoxA1 and FoxA2 is at least partially expressed and AFP is not expressed; and (4) obtaining a cell population in which one of FoxA1 and FoxA2 is at least partially expressed and Pdx-1 is not expressed.

Furthermore, in the culture method for causing differentiation of pluripotent mammalian cells according to an aspect of the present invention, a cell population differentiated into endoderm lineage cells obtained by the culture method described above is cultured in a culture medium including one kind or two or more kinds selected from the group consisting of FGF, BMP2, HGF, KGF, EGF, TGF-α, HB-EGF, VEGF, PDGF, DMSO, dexamethasone, oncostatin M, and insulin, to obtain a second cell population partially including cells expressing one of albumin (ALB) and α-fetoprotein (AFP).

In the culture method for causing differentiation of pluripotent mammalian cells according to an aspect of the present invention, it is preferable to culture the cell population in an atmosphere having an oxygen concentration of 4% or less.

The cell culture chamber described above is preferably a resin molding formed of one or a combination of two or more selected from the group consisting of acrylic resin, polylactic acid, polyglycolic acid, styrene resin, acrylic styrene copolymer resin, polycarbonate resin, polyester resin, polyvinyl alcohol resin, ethylene vinyl alcohol copolymer resin, thermoplastic elastomer, vinyl chloride resin, and silicon resin.

As for the microchambers described above, in a portion corresponding to 50% or more of an upper portion of each side wall formed in a height direction of the space structure of the microchambers, an angle formed between the bottom and a side surface of each side wall is preferably 80° to 90°.

The bottom of each of the microchambers described above preferably has a major axis that is in a range of 1 to 1.5 times greater than a minor axis of the bottom.

A surface treatment is preferably performed on a region in which the microchambers are formed. The surface treatment preferably includes one of: coating with an inorganic substance; coating with an extracellular matrix such as collagen or laminin; coating with a synthetic material; coating by plasma treatment; and providing concave-convex on a bottom surface of each of the microchambers, the concave-convex having a diameter in a range of 1 nm corresponding to a cell focal adhesion to 20 μm corresponding to a cell.

Advantageous Effects of Invention

The present invention provides a culture method for causing differentiation of pluripotent mammalian cells, which achieves control of embryoid body size and can induce differentiation in a state where the embryoid body size is controlled, by using a cell culture chamber including a plurality of microchambers formed on a surface, the cell culture chamber having a culture surface formed of spaces in which the microchambers have a bottom area of 100 μm$^2$ to 1 mm$^2$ and a depth of 10 μm to 500 μm.

DESCRIPTION OF EMBODIMENTS

Figure 1:
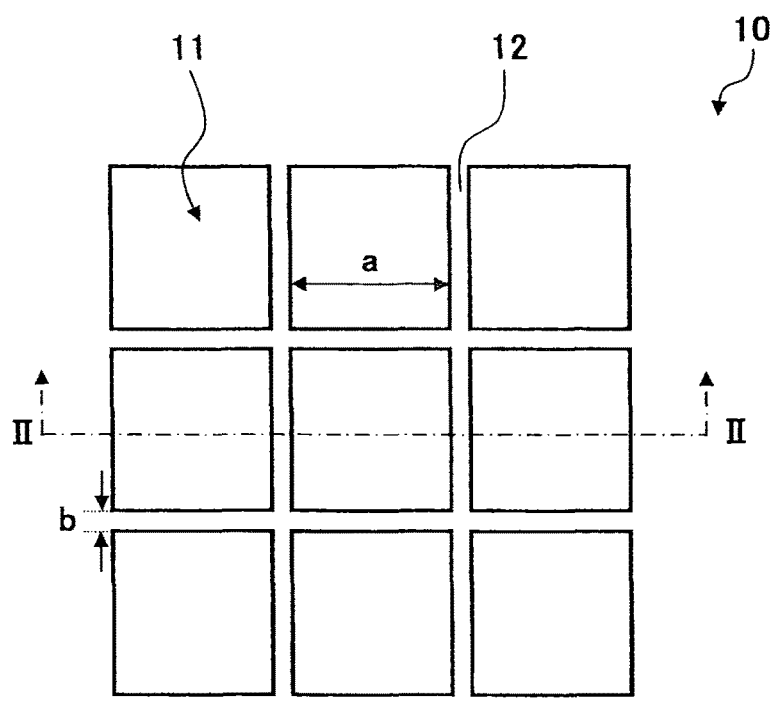
FIG. 1 is a plan view showing a structure of a cell culture chamber according to an embodiment of the present invention.

Hereinafter, an embodiment of the present invention will be described with reference to the drawings. However, the present invention is not limited to the embodiment described below. For clarity of explanation, the following description and the drawings are omitted and simplified as appropriate. The components having the same structure or function and corresponding parts in the drawings are denoted by the same reference numerals, and the description thereof is omitted.

Embodiment

First, a cell culture chamber according to an embodiment will be described. A cell culture method will be described thereafter.

1. Cell Culture Chamber

Figure 2:
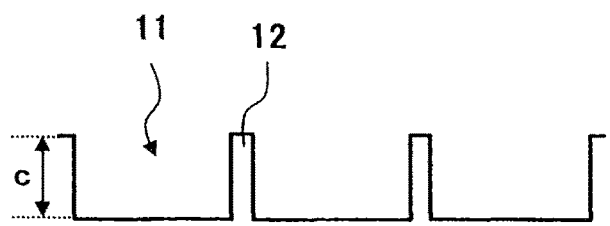
FIG. 2 is a sectional view taken along the line II-II of the cell culture chamber shown in FIG. 1.

FIG. 1 is a plan view showing a structure of a cell culture chamber according to this embodiment, and FIG. 2 is a sectional view taken along the line II-II of FIG. 1. As shown in FIG. 1, a cell culture chamber 10 includes microchambers 11 and side walls 12. The plurality of side walls 12 is formed in a net shape on the culture surface of the cell culture chamber 10, and spaces (micro-spaces) surrounded by the side walls 12 serve as the microchambers 11.

FIG. 1 shows a width "a" of the bottom of each of the microchambers 11, and a width "b" and a height "c" of each of the side walls 12 for partitioning the microchambers 11. The term "bottom area" herein described refers to a projected area which is formed when parallel light is irradiated to the bottom of the chamber from above in the direction perpendicular to the horizontal plane of the microchamber opening (the same plane as the top surfaces of the side walls 12). The area has a size of 100 µm$^2$ to 1 mm$^2$. For example, if the bottom of the microchamber is U-shaped, the bottom area has a shape formed by projecting parallel light incident on the bottom from above in the direction perpendicular to the opening plane. In the case of a circle or an ellipse, a major axis of a projected bottom is a distance between intersections of a long axis which runs through the center of gravity thereof and the circumference, and a minor axis of the projected bottom is a distance between intersections of a short axis which runs through the center of gravity thereof and the circumference. In the case of a polygon, the major axis and the minor axis of the projected bottom respectively correspond to a long axis and a short axis of an extrapolated circle or an extrapolated ellipse which is set so as to minimize the difference between areas of the polygon and the extrapolated circle or the extrapolated ellipse and which runs through all vertexes of the polygon. If an extrapolated circle or an extrapolated ellipse which runs through all vertexes of the polygon cannot be traced, the major axis and the minor axis respectively correspond to a long axis and a short axis of an approximate circle or an approximate ellipse which runs through the largest number of vertexes. When the size of the bottom is expressed using a width and a depth, the width and the depth are perpendicular to each other above the bottom.

The bottom shape of each of the microchambers 11 is not particularly limited, and various shapes other than a square, a circle, and a polygon can be employed. In cell culture for reproducing a liver function in vivo, the bottom area is preferably 0.01 mm$^2$ to 0.1 mm$^2$. In this case, the major axis of the bottom is preferably 1 to 1.5 times the minor axis thereof. Further, an isotropic shape is preferably used. If a square is employed, for example, in the case of forming an aggregate of embryoid bodies having an equivalent diameter of 100 µm, the length of one side thereof is preferably 100 µm to 300 µm. Further, in the case of forming an aggregate of embryoid bodies having an equivalent diameter of 500 µm, for example, the length of one side thereof is preferably 500 µm to 800 µm.

An angle formed between the horizontal plane and the side walls 12 of each of the microchambers 11 should be set to an angle at which cells are prevented from running on the micro chambers. Accordingly, 50% or more of an upper portion of a side surface preferably has an angle of 80° to 90°, and more preferably, 85° to 90°.

The height "c" of the side wall 12 may be set to such a value that prevents the cells to be cultured in the microchambers 11 from moving to the neighboring microchambers 11, and thus, the height "c" is preferably 10 µm to 500 µm. For example, in the case of forming an aggregate of embryoid bodies having an equivalent diameter of 100 µm, the height "c" of each side wall 12 is preferably 50 µm to 150 µm. Further, for example, in the case of forming an aggregate of embryoid bodies having an equivalent diameter of 500 µm, the height "c" is preferably 50 µm to 300 µm.

Figure 3:
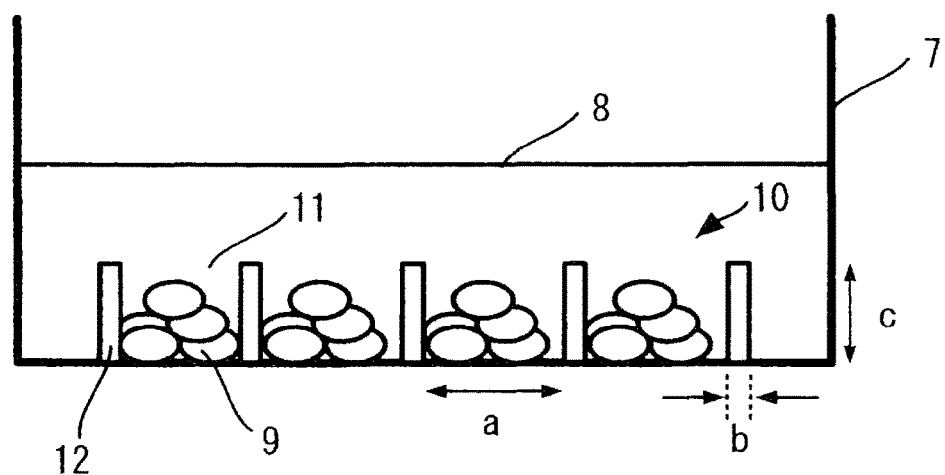
FIG. 3 is a schematic view showing a state where cells are cultured using the cell culture chamber shown in FIG. 1.

FIG. 3 is a schematic view showing a state where cells are cultured using the cell culture chamber shown in FIG. 1. FIG. 3 shows a perspective view of the cell culture chamber when viewed from a side surface. The cell culture chamber 10 is placed in a given petri dish or well plate 7, and the cell culture chamber 10 is filled with a culture medium 8. Cells 9 are cultured in the microchambers 11 which are formed so as to be surrounded by the side walls 12. FIG. 3 shows the width "a" of the bottom of each of the microchambers 11, and the width "b" and the height "c" of each of the side walls 12, as in FIGS. 1 and 2. The surface of each space formed of the bottom and the side walls 12 of each of the microchambers 11 is used as a culture surface. The cells 9 are cultured using the culture surface.

Figure 4:
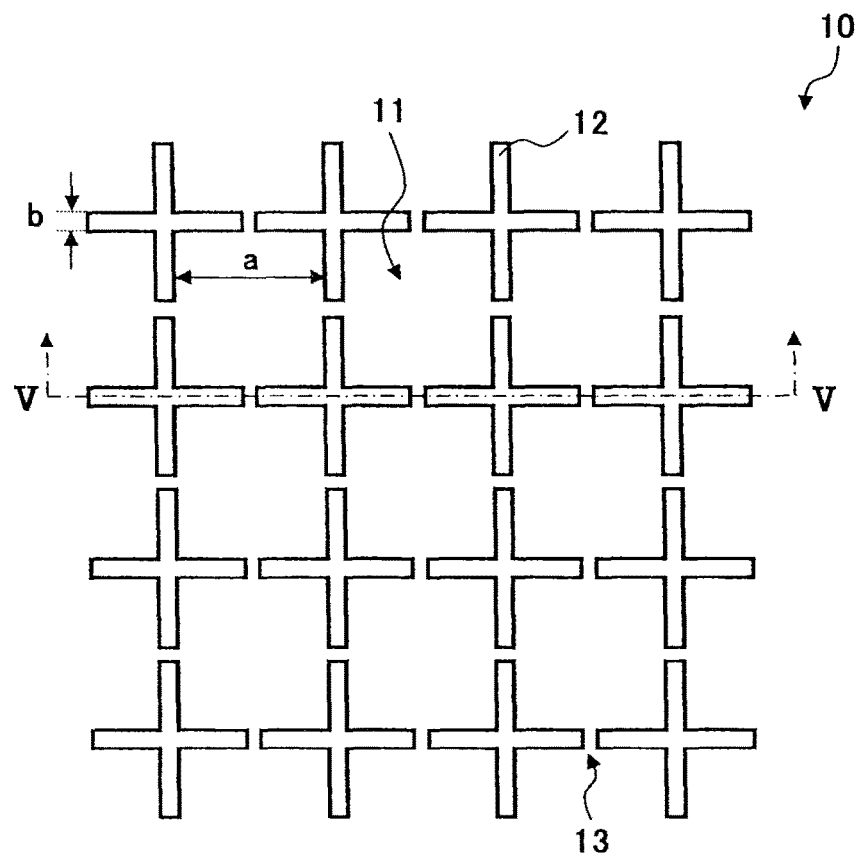
FIG. 4 is a plan view showing another structure of the cell culture chamber according to an embodiment of the present invention.
Figure 5:
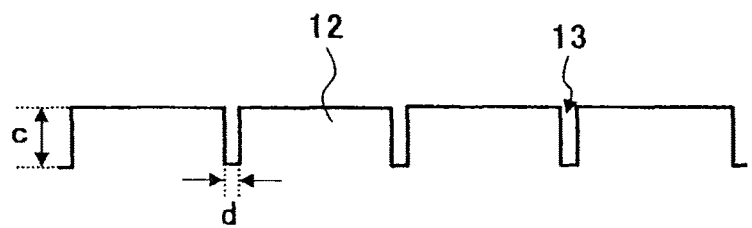
FIG. 5 is a sectional view taken along the line V-V of the cell culture chamber shown in FIG. 4.

Note that as shown in FIGS. 4 and 5, an opening 13 may be formed at a central portion of each side of the side walls 12 which are formed on four sides of each of the microchambers 11. A width "d" of the opening 13 for allowing communication between the neighboring microchambers 11 may be set to such a value that prevents the cells from moving from the microchamber 11, in which the cultured cells are first seeded, to the neighboring microchambers 11. For example, when the cultured cells have an equivalent diameter of 20 µm, the width "d" is preferably 5 to 15 µm. FIG. 4 is a plan view showing another structure of the cell culture chamber according to this embodiment. FIG. 5 is a sectional view taken along the line V-V of FIG. 4.

Figure 6:
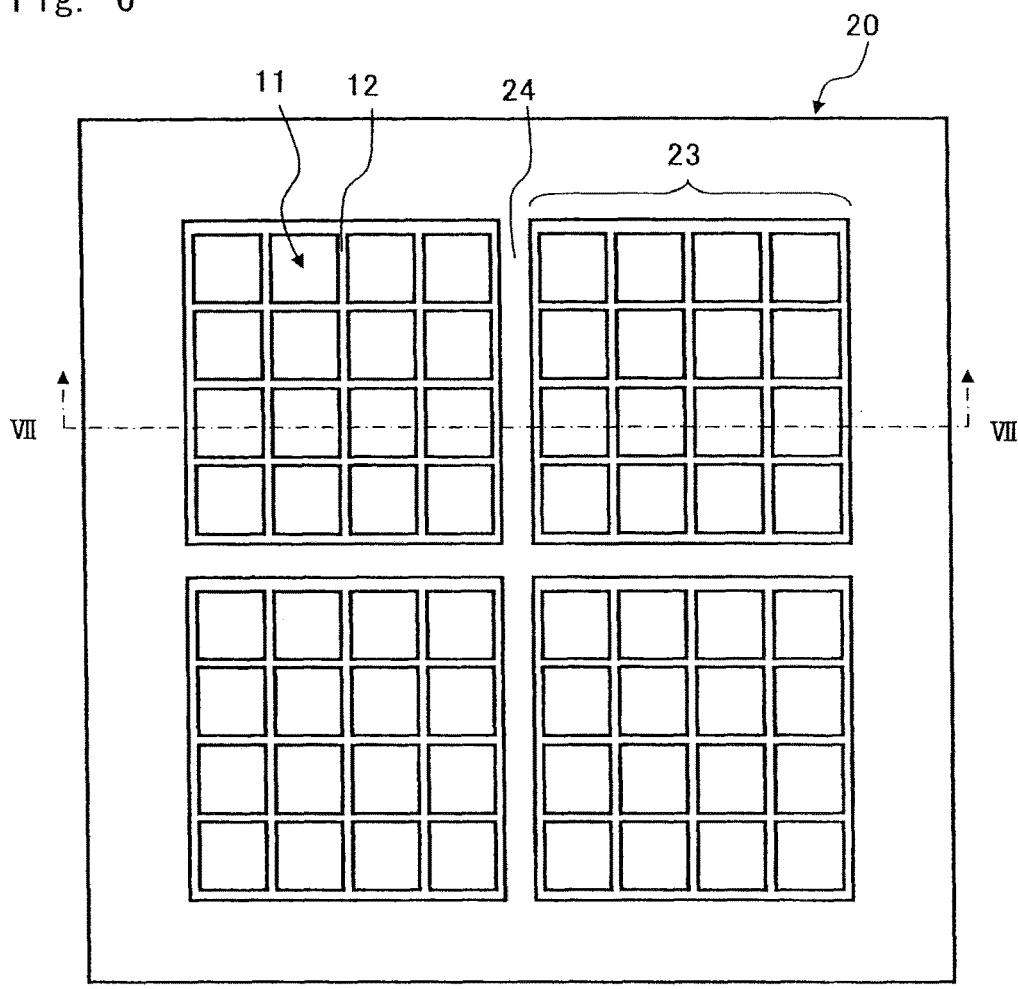
FIG. 6 is a plan view showing still another structure of the cell culture chamber according to an embodiment of the present invention.
Figure 7:
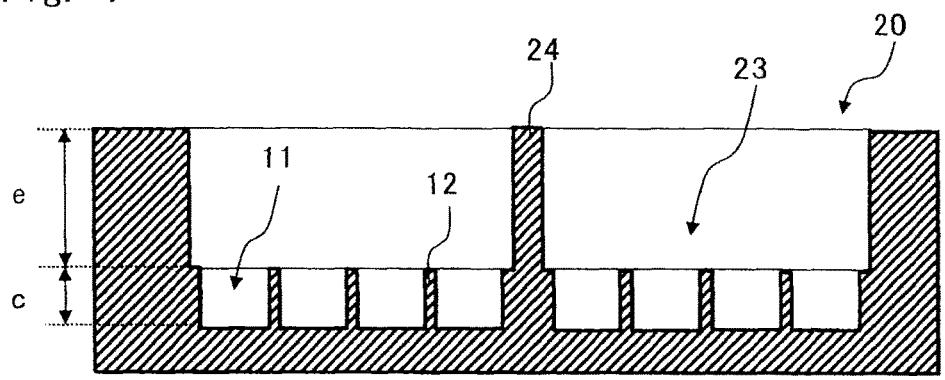
FIG. 7 is a sectional view taken along the line VII-VII of the cell culture chamber shown in FIG. 6.

As shown in FIGS. 6 and 7, the cell culture chamber according to this embodiment may have partitioned spots each made up of a predetermined number of microchambers. FIG. 6 is a plan view showing still another structure of the cell culture portion according to this embodiment. FIG. 7 is a sectional view taken along the line VII-VII of FIG. 6. FIGS. 6 and 7 show an example in which the microchamber structure shown in FIGS. 4 and 5 is used. FIG. 6 shows side walls 24 that partition the plurality of microchambers, and partitioned spots 23. A height "e" of each of the side walls 24 can be arbitrarily set to satisfy a capacity for storing a supernatant fluid such as culture solution or reaction solution without being dried. Since the side walls 24 are provided, different culture mediums can be used in each of the spots 23. Though FIGS. 6 and 7 show an exemplary structure including the side walls 24, a structure without the side walls 24 may also be employed.

A method for forming an concave-convex pattern on the cell culture chamber is not particularly limited, but methods such as transfer molding using a mold, three-dimensional stereolithography, precision machining, wet etching, dry etching, laser processing, and electrical discharge machining may be employed. It is preferable to appropriately select these production methods in view of the intended use, required processing accuracy, costs, and the like of the cell culture chamber.

As a specific example of the transfer molding method using a mold, a method for forming the concave-convex pattern by resin molding using a metal structure as a mold may be employed. This method is preferred because it is capable of reproducing the shape of the metal structure on a resin as the concave-convex pattern with a high transcription rate, and because the raw material cost can be reduced by using a general-purpose resin material. Such a method using a mold of a metal structure is superior in terms of low cost and satisfying high dimensional accuracy.

Examples of the method for producing the metal structure include plating treatment on a resist pattern produced by photolithography or a resin pattern produced by three-dimensional stereolithography, precision machining, wet etching, dry etching, laser processing, and electrical discharge machining. The methods may be appropriately selected in view of the intended use, required processing accuracy, costs, and the like.

Examples of the method for forming the concave-convex pattern on a resin using the metal structure, which is obtained as described above, as a mold, include injection molding, press molding, monomer casting, solvent casting, hot embossing, or roll transfer by extrusion molding. It is preferable to employ injection molding in view of its productivity and transcription property.

Materials for forming a cell culture chamber are not particularly limited as long as the materials have self-supporting properties. For example, synthetic resin, silicon, or glass may be employed. A transparent synthetic resin is preferably used as a material in view of costs and cell visibility under microscopic observation. Examples of the transparent synthetic resin include acrylic resins such as polymethylmethacrylate and methyl methacrylate-styrene copolymer, styrene resins such as polystyrene and acrylic styrene copolymer resin, olefin resin such as cycloolefin, ester resins such as polyethylene terephthalate, polylactic acid, and polyglycolic acid, silicone resin such as polydimethylsiloxane, polycarbonate resin, polyester resin, polyvinylalcohol resin, ethylene-vinylalcohol copolymer resin, thermoplastic elastomer, vinyl chloride resin, and silicon resin. These resins may contain various additives such as colorant, dispersing agent, and thickening agent, unless the transparency is impaired.

In the cell culture chamber, surface treatment may be performed on the surface side of the concave-convex pattern and a modified layer and/or a coating layer may be formed for the purpose of improving the hydrophilic properties, biocompatibility, cellular affinity, and the like of the chamber surface. A method for forming the modified layer is not particularly limited unless a method with which the self-supporting properties are impaired and a method causing extreme surface roughness of 100 μm or more are employed. Methods, for example, treatment by chemical reagent, solvent treatment, treatment by chemical reagent such as introduction of a graft polymer by surface graft polymerization, physical treatment such as corona discharge, ozone treatment, or plasma treatment may be employed. In addition, though a method for forming the coating layer is not particularly limited, methods, for example, dry coating such as sputtering or vapor deposition and wet coating such as inorganic material coating or polymer coating may be employed. In order to pour a culture solution without mixing air bubbles therein, it is desirable to impart the hydrophilic properties to the surface of the concave-convex pattern. As a method for forming a uniform hydrophilic membrane, inorganic vapor deposition is preferably employed.

When the cellular affinity is taken into consideration, it is more preferable to coat cytophilic proteins such as collagen, fibronectin, and laminin. In order to uniformly coat a collagen aqueous solution or the like, it is preferable to perform the coating after the above-mentioned hydrophilic membrane is formed. It is desirable to culture cells on an extracellular matrix surface by replicating the in vivo environment. Accordingly, it is particularly preferable to dispose an organic layer made of extracellular matrix suitable for cultured cells after an inorganic hydrophilic membrane is uniformly formed as described above.

It is also possible to employ a method in which concave-convex having a size of 1 nm to 20 μm, which is equivalent to a size in the range of a cell focal adhesion to a cultured cell, on the bottom surface of each microchamber. It is preferable to employ a method in which the hydrophilic treatment and the method for coating cytophilic proteins as described above are performed in combination on the surface.

The above-described surface treatment may be performed singly or appropriately combined as needed.

In a cell culture method using the cell culture chamber described above, an appropriate number of cells need to be seeded so that the cells are arranged exclusively within the microchambers for culturing cells, and morphologies and functions similar to those of the living body are developed within the space. A cell seeding density of $1.0 \times 10^2$ to $1.0 \times 10^6$ cells/cm$^2$ is preferably used and a cell seeding density of $1.0 \times 10^3$ to $1.0 \times 10^5$ cells/cm$^2$ is more preferably used. When each microchamber is a square which is 100 μm on a side, for example, a cell seeding density of $5.0 \times 10^3$ to $5.0 \times 10^5$ cells/cm$^2$ is preferably used.

Cells that are proliferated using a typical culture plate or culture dish having a flat culture surface may be used as pluripotent mammalian cells to be used. The cells may also be proliferated using the cell culture chamber described above.

Feeder cells are generally used for the cell proliferation described above. However, it is preferable not to use feeder cells in order to avoid contamination of other cells and simplify the operation.

The cell culture method using the cell culture chamber described above includes a process for forming an aggregate of embryoid bodies. In this case, feeder cells may be used, but it is more preferable not to use feeder cells in view of avoiding contamination of other cells and simplifying the operation.

2. Cell Culture Method

In this embodiment, a description is given of a culture method that cultures pluripotent mammalian cells to obtain a population of cells that are at least partially differentiated into endoderm lineage cells.

The following terms are herein used to explain the cell culture method.

The term "pluripotent" refers to an ability of a cell that can generate any type of cells other than cells supporting an embryonic structure.

The term "pluripotent cell" refers to a cell capable of at least developing into one of ectodermal, endodermal, and mesodermal cells.

The term "totipotent cell" refers to a cell capable of developing into all lineages of cells.

The term "embryonic stem cell (ES cell)" refers to a type of pluripotent cells. The ES cell is a cell derived from an embryo in early development and has an ability to proliferate and differentiate into various types of cells. The ES cell is established from an inner cell mass extracted from a blastocyst which is formed at a stage of a fertilized egg.

The term "induced pluripotent stem cell (iPS cell)" refers to a type of pluripotent cells. The iPS cell is a cell that can proliferate and differentiate into various types of cells, like the ES cell. The iPS cell can be produced from skin cells and the like.

The term "multipotent" refers to a cell that is not terminally differentiated. Similarly, the term "multipotent" refers to a cell that, without manipulation (i.e., nuclear transfer or dedifferentiation inducement), is incapable of forming differentiated cell types derived from all three germ layers (mesoderm, ectoderm, and endoderm), or in other words, is a cell that is partially differentiated.

The term "pluripotent human cell" encompasses pluripotent cells obtained from human embryos, fetuses, or adult tissues. The pluripotent human cell can be selected from the group consisting of an ES cell, an iPS cell, a human inner cell mass (ICM)/epiblast cell, a human primitive ectodermal cell, such as an early primitive ectodermal cell (EPL), a human primordial germ (EG) cell, and a human teratocarcinoma (EC) cell.

The term "endoderm" includes, but is not limited to, definitive endoderm, parietal endoderm, visceral endoderm, and mesendoderm cells. As used herein, the term "definitive endoderm" refers to early endoderm cells that have the capacity to differentiate into any or many of the endoderm cell types that are generated from the endoderm lineages in the embryo (i.e. pancreas, liver, lung, stomach, intestine, and thyroid). Definitive endodermal cells are multipotent. Therefore, the use of the term "definitive endoderm" in the context of the present invention means that the cell is at least more differentiated towards an endoderm cell type than the pluripotent cell from which it is derived. Also, as used herein, producing an endoderm cell encompasses the production of a cell culture that is enriched for endoderm cells.

The "definitive endoderm" cells are characterized by the expression of specific marker transcripts such as SOX17, with the concomitant absence of marker transcripts for AFP and thrombomodulin. Note that such cells can express MIX1, GATA4, HNFα, and HNF3b.

A crucial stage in early human development termed gastrulation occurs 2-3 weeks after fertilization. During gastrulation, the process of definitive endoderm formation begins with a cellular migration event in which mesendoderm cells (cells competent to form mesoderm or endoderm) migrate through a structure called the primitive streak. Definitive endoderm is derived from cells, which migrate through the anterior portion of the streak and through the node (a specialized structure at the anterior-most region of the streak). As migration occurs, definitive endoderm populates first the most anterior gut tube and culminates with the formation of the posterior end of the gut tube.

The term "differentiate" refers to the production of a cell type that is more differentiated than the cell type from which it is derived. The term therefore encompasses cell types that are partially and terminally differentiated.

In the case of referring to a cell, cell line, cell culture, or population of cells, the term "isolated" refers to being substantially separated from the natural source of the cells such that the cell, cell line, cell culture, or population of cells are capable of being cultured in vitro. In addition, the term "isolating" is used to refer to the physical selection of one or more cells out of a group of two or more cells. In this case, these cells are selected based on cell morphology and/or the expression of various markers.

The term "express" refers to the transcription of a polynucleotide or translation of a polypeptide in a cell, such that levels of the molecule are measurably higher in a cell that expresses the molecule than they are in a cell that does not express the molecule. Methods to measure the expression of a molecule are well known to those of ordinary skill in the art, and include, without limitation, Northern blotting, RT-PCR, in situ hybridization, Western blotting, and immunostaining.

The term "adherent culture" refers to a cell culture system whereby cells are cultured on a solid surface, which may in turn be coated with a solid substrate that may in turn be coated with another surface coat of a substrate, such as those listed below, or any other chemical or biological material that allows the cells to proliferate or be stabilized in culture. The cells may or may not tightly adhere to the solid surface or to the substrate.

The term "Sox17" refers to a marker indicating an endoderm lineage cell. It is known that Sox17 is a transcription control factor including a DNA-binding domain and is a member of the Sry-related high mobility group box (Sox) family that is closely related to the fate determination of stem cells, and is thus required to form and maintain the endoderm.
Reference: Hudson, C., Clements, D., Friday, R. V., Stott, D., and Woodland, H. R. (1997). Xsox17α and -β mediate endoderm formation in *Xenopus*. Cell 91, 397-405.

Each of the terms "FoxA1" and "FoxA2" refers to a member of the Human Forkhead-box (FOX) gene family, and is said to be expressed at a stage prior to the differentiation into pancreatic cells or hepatic cells. That is, the cells in which these genes are expressed are defined as cells intermediate between endoderm lineage cells and mature tissue cells.

The term "Pdx-1" is known as a gene to be expressed in a pancreatic cell and serves as a marker indicating a pancreatic cell.

The term "AFP" is known as a gene to be expressed in a hepatic cell and serves as a marker indicating a hepatic cell.

EXAMPLES

Example 1

1. Process for Controlling Mouse iPS Cells

A cell culture chamber including microchambers in which spaces having a height of 50 μm, a width of 100 μm, and a length of 100 μm are regularly arranged on a culture bottom surface was used. Mouse iPS cells were seeded at a density of $0.5 \times 10^5/cm^2$ and were cultured in a DMEM (manufactured by GIBCO, Inc.) culture medium including 18% FBS, 2-mercaptoethanol (110 mM), and 500 U/ml leukemia inhibitory factor, for three days. The culture medium was changed once every 24 hours.

2. Process for Preparing an Aggregate of Embryoid Bodies (EB Culture)

The culture medium was replaced with a DMEM-F12 (manufactured by GIBCO, Inc.) culture medium including 15% FBS, 1% nonessential amino acids, 1% nucleosides, 1% penicillin/streptomycin, and 1% glutamic acid, and the culture was carried out for two days. The culture medium was changed once a day.

3. Process for Preparing Endoderm Lineage Cells

The culture medium was replaced with a DMEM-F12 (manufactured by GIBCO, Inc.) culture medium including 1% FBS, 1% nonessential amino acids, 1% nucleosides, 1% penicillin/streptomycin, 1% glutamic acid, 3% BSA, 100 ng/ml FGF-2, and 100 ng/ml Activin-A, and the culture was carried out for three days. The culture medium was changed once every 12 hours.

4. Process for Preparing AFP and ALB Positive Cells

The culture medium was replaced with a DMEM-F12 culture medium including 10-15% FBS, 1% nonessential amino acid, 1% nucleosides, 1% penicillin/streptomycin, 1% glutamic, 50 ng/ml HGF, and 1% DMSO, and the culture was carried out for eight days. The culture medium was changed once every 12 hours. Further, the culture was carried out for three days in a DMEM-F12 culture medium including 10-15% FBS, 1% nonessential amino acid, 1% penicillin/streptomycin, 1% glutamic acid, 100 ng/ml dHGF, and $10^{-7}$M dexamethasone. The culture medium was changed once every 12 hours.

Comparative Example 1

0. Process for Controlling Feeder Cells

In a cell culture dish made of plastic with a size of φ6 cm and having a flat culture bottom surface, feeder cells (primary mouse embryo fibroblasts) (P-MEF-CF manufactured by Dainippon Pharmaceutical Co., Ltd.) were cultured for eight hours in a DMEM culture medium including 10% FBS, 4500 mg/L-glucose, 2 mM L-glutamine, and 1% penicillin/streptomycin.

1. Control of Mouse iPS Cells (2 Processes)

1.1 Cell Seeding Process

In the culture dish obtained in the above-mentioned process 0, mouse iPS cells were seeded at a density of $0.5 \times 10^5/cm^2$ and were cultured for three days in a DMEM (manufactured by GIBCO, Inc.) culture medium including 18% FBS, 2-mercaptoethanol (110 mM), and 500 U/ml leukemia inhibitory factor. The culture medium was changed once every 24 hours.

1.2 Cell Recovery Process

After the culture medium used in the process 1.1 was removed through cleaning with PBS, the iPS cells were separated from the feeder cells by using a 0.25% trypsin/EDTA solution.

2. Process for Preparing an Aggregate of Embryoid Bodies (EB Culture)

The cells obtained in the process 1.2 were seeded in a culture dish made of plastic with a size of φ6 cm and having a flat culture bottom surface. A DMEM-F12 (manufactured by GIBCO, Inc.) culture medium including 15% FBS, 1% nonessential amino acids, 1% nucleosides, 1% penicillin/streptomycin, and 1% glutamic acid was used as the culture medium and the culture was carried out for two days. The culture medium was changed once a day.

3. Process for Preparing Endoderm Lineage Cells

The culture medium was replaced with a DMEM-F12 (manufactured by GIBCO, Inc.) culture medium including 1% FBS, 1% nonessential amino acids, 1% nucleosides, 1% penicillin/streptomycin, 1% glutamic acid, 3% BSA, 100 ng/ml FGF-2, and 100 ng/ml Activin-A, and the culture was carried out for three days. The culture medium was changed once every 12 hours.

4. Process for Preparing AFP and ALB Positive Cells

The culture medium was replaced with a DMEM-F12 culture medium including 10-15% FBS, 1% nonessential amino acid, 1% nucleosides, 1% penicillin/streptomycin, 1% glutamic acid, 50 ng/ml HGF, and 1% DMSO, and the culture was carried out for eight days. The culture medium was changed once every 12 hours. Further, the culture medium was replaced with a DMEM-F12 culture medium including 10-15% FBS, 1% nonessential amino acid, 1% penicillin/streptomycin, 1% glutamic acid, 100 ng/ml dHGF, and $10^{-7}$ M dexamethasone, and the culture was carried out for three days. The culture medium was changed once every 12 hours.

[Analysis]

An analysis was made by real-time PCR method. The iPS cells before use for the above-mentioned process 1 and the cells obtained after the above-mentioned culture process 4 were retrieved, and a quantitative analysis of mRNA relative to AFP, ALB, and GAPDH was made. The mRNA expression levels of ALB and AFP were calculated as values relative to GAPDH.

[Result]

Shown below are relative values assuming that each gene expression level of the iPS cells before use for the above-mentioned process 1 is "1".

TABLE 1

|  | iPS | Comparative Example 1 | Example 1 |
|---|---|---|---|
| AFP/GAPDH | 1 | 157.54 | 611.22 |
| ALB/GAPDH | 1 | 274.15 | 20170.13 |

When the cells were differentiated into endoderm lineage cells by the method of Example 1 and then differentiated into hepatic cells, the gene expression levels of AFP and ALB, which are liver specific markers, showed higher values that are respectively 1.7 times and 33 times higher than those of Comparative Example.

Example 2

Differentiation induction of human iPS cells using a culture plate having microchambers 0. Process for Controlling Feeder Cells In a cell culture dish made of plastic with a size of φ6 cm and having a flat culture bottom surface, feeder cells (primary mouse embryo fibroblasts) were cultured for eight hours in a DMEM culture medium including 10% FBS, 4500 mg/L-glucose, 2 mM L-glutamine, and 1% penicillin/streptomycin.

1. Process for Controlling Human iPS Cells

A human iPS cell line 201B7 (RIKEN BRC No.: HPS0001) was maintained on mouse fibroblasts (MEFs) by using a culture medium including DMEM/F12+20% KSR+bFGF.

2. Process for Preparing Embryonic Endodermal Cells

In a cell culture chamber including microchambers coated with Matrigel, in which spaces having a height of 50 μm, a width of 100 μm, and a length of 100 μm are regularly arranged on a culture bottom surface, human iPS cells dispersed into single cells were seeded and cultured for 24 hours by using a differentiation-inducing culture medium obtained by adding B27 to RPMI1640. After 24 hours, the culture medium was replaced with a culture medium obtained by adding human type Activin to a differentiation-inducing culture medium, and the culture was carried out for six days. The culture medium was changed once every two days.

3. Process for Preparing Hepatocyte Lineage Cells (Process for Preparing AFP and HNF4A Positive Cells)

After the operation of "2. Process for preparing embryonic endodermal cells" in Example 2 was carried out, the culture medium was replaced with a culture medium obtained by adding 10 ng bFGF and 20 ng/ml hBMP4 to a differentiation-inducing culture medium, and the culture was carried out for three days. The culture medium was changed once every two days.

Then, the culture medium was replaced with a culture medium obtained by adding 40 ng hHGF to a differentiation-inducing culture medium, and the culture was further carried out for four days. The culture medium was changed once every two days.

Comparative Example 2

Differentiation induction of human iPS cells using a flat culture plate

0. Process for Controlling Feeder Cells

In a cell culture dish made of plastic with a size of φ6 cm and having a flat cell culture dish, feeder cells (primary mouse embryo fibroblasts) were cultured for eight hours in a DMEM culture medium including 10% FBS, 4500 mg/L-glucose, 2 mM L-glutamine, and 1% penicillin/streptomycin.

1. Process for Controlling Human iPS Cells

A human iPS cell line 201B7 (RIKEN BRC No.: HPS0001) was maintained on mouse fibroblasts (MEFs) by using a culture medium including DMEM/F12+20% KSR+bFGF.

2. Process for Preparing Embryonic Endodermal Cells

In a cell culture chamber coated with Matrigel and having a flat culture bottom surface, human iPS cells dispersed into single cells were seeded and cultured for 24 hours by using a differentiation-inducing culture medium obtained by adding B27 to RPMI1640. After 24 hours, the culture medium was replaced with a culture medium obtained by adding human type Activin to a differentiation-inducing culture medium, and the culture was carried out for six days. The culture medium was changed once every two days.

3. Process for Preparing Hepatocyte Lineage Cells (Process for Preparing AFP and HNF4A Positive Cells)

After the the operation of "2. Process for preparing embryonic endodermal cells" in Comparative Example 2 was carried out, the culture medium was replaced with a culture medium obtained by adding 10 ng bFGF and 20 ng/ml hBMP4 to a differentiation-inducing culture medium, and the culture was carried out for three days. The culture medium was changed once every two days.

Then, the culture medium was replaced with a culture medium obtained by adding 40 ng hHGF to a differentiation-inducing culture medium, and the culture was further carried out for four days. The culture medium was changed once every two days.

[Analysis]

The gene expression levels of markers Sox17 and CXCR4 of definitive endodermal cells were analyzed by Quantitative PCR using the cells obtained in "2. Process for preparing embryonic endodermal cells" of Example 2 and "2. Process for preparing embryonic endodermal cells" of Comparative Example 2. The expression levels of HNF4A and AFP markers of hepatocyte lineage cells were analyzed by Quantitative PCR using the cells obtained in "3. Process for preparing hepatocyte lineage cells" of Example 2 and "3. Process for preparing hepatocyte lineage cells" of Comparative Example 2. Values are expressed as relative values assuming that the expression level of each marker in Comparative Example 2 is "1".

[Result]

Table 2 shows the result of an analysis of the presence or absence of differentiation induction into embryonic endodermal cells. Here, SOX17 and CXCR4 are markers of embryonic endoderm, and AFP is a marker of hepatocyte lineage cells. The stages of "2. Process for preparing embryonic endodermal cells" of Example 2 and "2. Process for preparing embryonic endodermal cells" of Comparative Example 2 correspond to the process for causing differentiation into embryonic endodermal cells. Accordingly, it can be said that efficient differentiation into embryonic endodermal cells was observed at higher expression levels of SOX17 and CXCR4 and at a lower expression level of AFP.

TABLE 2

|  |  | Example 2 | Comparative Example 2 |
|---|---|---|---|
| Marker of embryonic endodermal cells | SOX17 | 5.57 ± 0.167 | 1 ± 0.058 |
|  | CXCR4 | 1.71 ± 0.039 | 1 ± 0.040 |

TABLE 2-continued

|  |  | Example 2 | Comparative Example 2 |
|---|---|---|---|
| Marker of hepatocyte lineage cells | AFP | Detection limit or lower | Detection limit or lower |

Table 3 shows the result of an analysis of the presence or absence of differentiation induction into hepatocyte lineage cells. Here, SOX17 is a marker specific to embryonic endodermal cells, and HNF4A and AFP are markers specific to hepatocyte lineage cells. The stages of "3. Process for preparing hepatocyte lineage cells" of Example 2 and "3. Process for preparing hepatocyte lineage cells" of Comparative Example 2 correspond to the process for causing differentiation into hepatocyte lineage cells. Accordingly, it can be said that efficient differentiation into hepatocyte lineage cells was observed at a lower expression level of SOX17 and at higher expression levels of HNF4A and AFP.

TABLE 3

|  |  | Example 2 | Comparative Example 2 |
|---|---|---|---|
| Marker of hepatocyte lineage cells | HNF4A | 2.24 ± 0.096 | 1 ± 0.064 |
|  | AFP | 22.46 ± 0.626 | 1 ± 0.050 |
| Marker of embryonic endodermal cells | SOX17 | 0.85 ± 0.029 | 1 ± 0.047 |

Table 4 shows the rate of decrease in expression level under the respective culture conditions, as a result of comparison between the gene expression level of SOX17 obtained after differentiation induction into hepatic cell lineages shown in Table 3 and the gene expression level of SOX17 obtained after differentiation induction into embryonic endodermal cells shown in Table 2.

TABLE 4

|  |  | Example 2 | Comparative Example 2 |
|---|---|---|---|
| Marker of embryonic endodermal cells | SOX17 | 0.014 ± 0.004 | 0.089 ± 0.004 |

In Example 2, the expression levels of markers SOX17 and CXCR4 specific to embryonic endodermal cells show higher values that are respectively about 5 times and 1.7 times higher than those of Comparative Example 2, and the marker of hepatocyte lineage cells is hardly expressed. That is, Example 2 (cell culture chamber including microchambers) enables efficient differentiation into embryonic endodermal cells.

In Example 2, the expression levels of markers HNF4A and AFP specific to hepatocyte lineage cells show higher values that are respectively about twice and 22 times as high as those of Comparative Example 2, and the expression level of the marker of hepatocyte lineage cells is high. Further, as shown in Table 4, the value of SOX17 obtained after the differentiation into hepatocyte lineage cells in Example 2 is one-tenth of that in Comparative Example 2. Accordingly, it can be said that the ratio of remaining embryonic endodermal cells to the cells obtained after the differentiation into hepatocyte lineage cells is small. That is, Example 2 (cell culture chamber including microchambers) enables efficient differentiation into hepatic cells which are embryonic endoderm lineage cells.

Note that the present invention is not limited to the above embodiment, but can be modified as necessary without departing from the scope of the present invention.

This application is based upon and claims the benefit of priority from Japanese patent application No. 2010-066324, filed on Mar. 23, 2010, the disclosure of which is incorporated herein in its entirety by reference.

REFERENCE SIGNS LIST

7 PETRI DISH OR WELL PLATE
8 CULTURE MEDIUM
9 CELL
10 CELL CULTURE CHAMBER
11 MICROCHAMBER
12 SIDE WALL
13 OPENING
23 SPOT
24 SIDE WALL OF SPOT

The invention claimed is:

1. A method for differentiating pluripotent mammalian stem cells into a population of hepatic cells, the method comprising: culturing pluripotent mammalian stem cells selected from the group consisting of mouse embryonic stem cells, human embryonic stem cells, mouse induced pluripotent stem cells and human induced pluripotent stem cells, wherein the culturing is performed on a cell culture chamber comprising a plurality of microchambers formed on a culture surface, the cell culture chamber having the culture surface formed of spaces, wherein a space structure of each microchamber has a height of 10 μm to 500 μm and a bottom area of 100 μm² to 0.1 mm²; and wherein the culturing comprises seeding the pluripotent mammalian stem cells that were not maintained on mouse fibroblasts or feeder cells into a culture medium in the cell culture chamber; replacing the culture medium with an embryoid bodies (EB) culture medium to prepare an aggregate of embryoid bodies from the pluripotent mammalian stem cells in the microchambers; and replacing the EB culture medium with culture medium comprising Activin-A to prepare a population of endoderm lineage cells from the aggregate of embryoid bodies in the microchambers; and replacing the culture medium comprising Activin-A with culture medium comprising bFGF and hBMP4 to prepare a population of hepatocyte lineage cells, then further replacing the culture medium comprising bFGF and hBMP4 with culture medium comprising hHGF to prepare a population of hepatic cells.

2. The method of claim 1, wherein 1 to 3×10⁵ pluripotent mammalian stem cells are seeded in at least one of the microchambers to obtain the population of hepatic cells.

3. The method of claim 1, wherein the culture medium comprising Activin-A further comprises another TGF-β family member, an FGF family member, a PI3-kinase signaling pathway inhibitor, or any mixture thereof.

4. The method of claim 3, wherein the culture medium comprises the TGF-β family member and wherein the TGF-β family member is selected from Nodal, Activin B, TGF-β, BMP2, BMP4, or any mixture thereof.

5. The method of claim 3, wherein the culture medium comprises the FGF family member and wherein the FGF family member is selected from b-FGF, FGF-4, FGF-2, or any mixture thereof.

6. The method of claim 3, wherein the culture medium comprises the PI3-kinase signaling pathway inhibitor and wherein the PI3-kinase signaling pathway inhibitor is selected from LY294002, rapamycin, wortmannin, lithium chloride, Akt inhibitor I, Akt inhibitor II, Akt inhibitor III, NL-71-101, or any mixture thereof.

7. The method of claim 1, wherein the population of endoderm lineage cells partially expresses SOX17, but does not express Pdx-1.

8. The method of claim 1, wherein the population of hepatocyte lineage cells partially expresses one of FoxA1 and FoxA2, but does not express Pdx-1.

9. The method of claim 1, wherein the culturing is performed on a cell culture chamber comprising a plurality of microchambers formed on a culture surface in an atmosphere comprising an oxygen concentration of 4% or less.

10. The method of claim 1, wherein the cell culture chamber is a resin molding comprising acrylic resin, polylactic acid, polyglycolic acid, styrene resin, acrylic styrene copolymer resin, polycarbonate resin, polyester resin, polyvinyl alcohol resin, ethylene vinyl alcohol copolymer resin, thermoplastic elastomer, vinyl chloride resin, silicon resin, or any mixture thereof.

11. The method of claim 1, wherein in a portion corresponding to 50% or more of an upper portion of each side wall formed in a height direction of the space structure of the microchambers, an angle of 80° to 90° between the bottom of the microchamber and a side surface of each side wall is formed.

12. The method of claim 1, wherein a bottom of each microchamber has a major axis that is in a range of 1 to 1.5 times greater than a minor axis of the bottom.

13. The method of claim 1, further comprising surface treating a region in which the microchambers are formed.

14. The method of claim 13, wherein the surface treatment comprises coating the region with an inorganic substance.

15. The method of claim 13, wherein the surface treatment comprises coating the region with an extracellular matrix, selected from collagen or laminin.

16. The method of claim 13, wherein the surface treatment comprises coating the region with a synthetic material.

17. The method of claim 13, wherein the surface treatment comprises coating the region by plasma treatment.

18. The method of claim 13, wherein each microchamber comprises a concave-convex bottom surface, the concave-convex bottom surface having a diameter in a range of 1 nm corresponding to a cell focal adhesion to 20 μm corresponding to a cell.

19. The method of claim 2, wherein in a portion corresponding to 50% or more of an upper portion of each side wall formed in a height direction of the space structure of the microchambers, an angle of 80° to 90° between the bottom of the microchamber and a side surface of each side wall is formed.

20. The method of claim 2, wherein a bottom of each microchamber has a major axis that is in a range of 1 to 1.5 times greater than a minor axis of the bottom.

21. The method of claim 2, further comprising surface treating a region in which the microchambers are formed.

22. A method for culturing pluripotent mammalian stem cells into a population of hepatic cells, the method comprising: seeding the pluripotent mammalian stem cells selected from the group consisting of mouse embryonic stem cells, human embryonic stem cells, mouse induced pluripotent stem cells, and human induced pluripotent stem cells, in a cell culture chamber having a culture surface and a plurality of microchambers formed on the culture surface; forming an aggregate of embryoid bodies from the pluripotent mammalian stem cells in the microchamber; culturing the aggregate of embryoid bodies in a culture medium in the microchamber; wherein the culture medium comprises a TGF-β family, a PI3-kinase signaling pathway inhibitor, or a combination thereof; replacing the culture medium with culture medium including Activin-A to prepare endoderm lineage cells from the aggregate of embryoid bodies in the microchamber; and replacing the culture medium including Activin-A with culture medium including bFGF and hBMP4, then further replacing the culture medium including bFGF and hBMP4 with culture medium including hHGF to prepare a population of hepatic cells; wherein each microchamber has a space structure having a height of 10 μm to 500 μm and a bottom area of 100 μm$^2$ to 0.1 mm$^2$.

23. The method according to claim 22, wherein the cell culture chamber is composed of a resin molding formed from at least one of polyglycolic acid, acrylic styrene copolymer resin, polyester resin, polyvinyl alcohol resin, ethylene vinyl alcohol copolymer resin, thermoplastic elastomer and vinyl chloride resin.

\* \* \* \* \*